US009084753B2

(12) United States Patent
Rich

(10) Patent No.: US 9,084,753 B2
(45) Date of Patent: Jul. 21, 2015

(54) USES FOR QUATERNARY AMMONIUM ANTICHOLINERGIC MUSCARINIC RECEPTOR ANTAGONISTS IN PATIENTS BEING TREATED FOR COGNITIVE IMPAIRMENT OR ACUTE DELIRIUM

(76) Inventor: Steven A. Rich, Canandaigua, NY (US)

( * ) Notice: Subject to any disclaimer, the term of this patent is extended or adjusted under 35 U.S.C. 154(b) by 565 days.

(21) Appl. No.: 13/325,371

(22) Filed: Dec. 14, 2011

(65) Prior Publication Data

US 2012/0088785 A1    Apr. 12, 2012

Related U.S. Application Data

(62) Division of application No. 11/935,483, filed on Nov. 6, 2007, now Pat. No. 8,097,633.

(60) Provisional application No. 60/865,893, filed on Nov. 15, 2006.

(51) Int. Cl.
| | |
|---|---|
| *A61K 31/14* | (2006.01) |
| *A61K 31/401* | (2006.01) |
| *A61K 31/403* | (2006.01) |
| *A61K 31/40* | (2006.01) |
| *A61K 31/135* | (2006.01) |
| *A61K 31/4015* | (2006.01) |
| *A61K 31/438* | (2006.01) |

(52) U.S. Cl.
CPC ........... *A61K 31/135* (2013.01); *A61K 31/4015* (2013.01); *A61K 31/438* (2013.01)

(58) Field of Classification Search
CPC .............................. A61K 31/14; A61K 31/40
See application file for complete search history.

(56) References Cited

U.S. PATENT DOCUMENTS

| | | | |
|---|---|---|---|
| 5,346,906 | A | 9/1994 | Baker et al. |
| 5,861,431 | A | 1/1999 | Hildebrand et al. |
| 6,063,808 | A | 5/2000 | Fabiano et al. |
| 6,204,285 | B1 | 3/2001 | Fabiano et al. |
| 7,091,236 | B1 | 8/2006 | Roberts et al. |
| 2004/0082644 | A1 | 4/2004 | Korsten |
| 2006/0018839 | A1 | 1/2006 | Ieni et al. |
| 2006/0142241 | A1 | 6/2006 | Yoo |

OTHER PUBLICATIONS

Verdejo et al. Anales de Medicina, 1992, vol. 9, No. 3, abstract.*
Carnahan et al. J. Am. Geriatric. Soc., 2004, vol. 52, No. 12, abstract.*
McKeith et al. The Lancet, 2000, vol. 356, pp. 2031-2036.
Defilippi and Crisman, "Drug Interactions with Cholinesterase Inhibitors". Drugs Aging 2003; 20(6):437-444.
Edwards and O'Connor. "Risk of delirium with concomitant use of tolterodine and and acetycholinesterase inhibitors". J Amer Geriatric Society, 2002;50 (6);1165-6.
Gill S et al. "A Prescribing Cascade Involving Cholinesterase Inhibitors and Anticholinergic Drugs". Arch Intern Med 2005;165:808-813.
Johnell and Fastbom. "Concurrent Use of Anticholinergic Drugs and Cholinesterase Inhibitors", Drugs Aging 2008;25 (10);871-877.
Lewy Body Dementia Association, Inc., treatment options page, http://www.lbda.org/content/treatment-options, at least as early as Apr. 10, 2015.
Lu and Tune, "Chronic Exposure to Anticholinergic Medications Adversely Affects the Course of Alzheimer Disease", Am J Geriatr Psychiatry 11:4, Jul.-Aug. 2003, pp. 458-461.
Teramura-Gronbladet al. "Use of Anticholinergic Drugs and Cholinesterase Inhibitors and Their Association with Psychological Well-Being Among Frail Older Adults in Residential Care Facilities." Ann Pharmacotherapy 2011;45:596-602.
Ray, P.G., et al. Central Anticholinergic Hypersensitivity in Aging, Journal of Geriatric Psychiatry and Neurology, vol. 5, Apr.-Jun. 1992, p. 72-77.
Robinul® glycopyrrolate tablets Product Information Sheet, Rev. Apr. 2010.
CUVPOSA glycopyrrolate oral solution Product Information Sheet, Rev. Jul. 2010.
Tsao, J.W. and Hellman, K.M., Transient Memory Impairment and Hallucinations Associated with Tolterodine Use, New England Journal of Medicine, vol. 349 (23), Dec. 4, 2003, p. 2274-2275.
Rudolph, J.L, et al., The Anticholinergic Risk Scale and Anticholinergic Adverse Effects in Older Persons, Arch Intern Med, vol. 168 (No. 5), Mar. 10, 2008.

(Continued)

*Primary Examiner* — Samira Jean-Louis
(74) *Attorney, Agent, or Firm* — Brown & Michaels, PC

(57) ABSTRACT

A method for treating the adverse effects of acetyl-cholinesterase inhibitors used in the treatment of cognitive disorders such as acute delirium and cognitive impairment in elderly human patients. The administration of a clinically effective amount of a quaternary ammonium anti-cholinergic muscarinic receptor antagonist having very low lipid solubility substantially eliminates the adverse effects of urinary and/or fecal incontinence, nausea, bradycardia, bronchorrhea or brochospasm caused by the acetyl-cholinesterase inhibitors, without affecting the beneficial activity of the acetyl-cholinesterase inhibitors. This permits the administration of the optimum effective dosing of acetyl-cholinesterase inhibitors to provide maximum benefit to the patient with the added benefit of reducing or eliminating the unwanted side effects of fecal and urinary incontinence. Further, the combination of rivastigmine and glycopyrrolate has been effective in significantly improving cognitive function in patients suffering from acute dementia or cognitive impairment.

20 Claims, No Drawings

(56) References Cited

OTHER PUBLICATIONS

Sink, K.M., et al., Dual Use of Bladder Anticholinergics and Cholinesterase Inhibitors: Long-Term Functional and Cognitive Outcomes, JAGS, 56:847-853, 2008.

Roe, C.M., et al., Use of Anticholinergic Medications by Older Adults with Dementia, JAGS, 50:836-842, 2002.

Terry, A.V. and Buccafusco, J.J., The Cholinergic Hypothesis of Age and Alzheimer's Disease-Related Cognitive Deficits: Recent Challenges and Their Implications for Novel Drug Development, JPET 306(3):821-827, 2003.

Oken, R.J., Antihistamines, a Possible Risk Factor for Alzheimer's Disease, Medical Hypotheses (1995) 44, 47-48.

Kay, G.G. and Ebinger, U., Preserving cognitive function for patients with overactive bladder: evidence for a differential effect with darifenacin, Int J Clin Pract, Nov. 2008, 62, 11, 1792-1800.

Janos, A.L., et al., Overactive bladder medicines and cognitive testing, Int J Clin Pract, Nov. 2008, 62, 11, 1637-1642.

Kay, G.G., et al., Antimuscarinic Drugs for Overactive Bladder and Their Potential Effects on Cognitive Function in Older Patients, JAGS 53:2195-2201, 2005.

Gish, P., et al., Memorandum: Age-dependent manifestations of central anticholinergic effects, Department of Health and Human Services Public Health Service Food and Drug Administration Center for Drug Evaluation and Research, Mar. 5, 2007.

Jewart, R.D., et al., Cognitive, Behavioral and Physiological Changes in Alzheimer Disease Patients as a Function of Incontinence Medications, Am J Geriatr Psychiatry 13:4, Apr. 2005.

Drinka, P.J., Antimuscarinic Drugs for Overactive Bladder and Their Potential Effects on Cognitive Function in Older Patients, JAGS 54:1004-1005, 2006.

Carnahan, R.M., et al., The Concurrent Use of Anticholinergics and Cholinesterase Inhibitors: Rare Event or Common Practice? JAGS 52:2082-2087, 2004.

Chew, M.L., et al., Serum Anticholinergic Activity and Cognition in Patients with Moderate-to-Severe Dementia, Am J Geriatr Psychiatry 13:6, Jun. 2005.

Ancelin, M.L., et al., Non-degenerative mild cognitive impairment in elderly people and use of anticholinergic drugs: longitudinal cohort study, BMJ, doi:10.1136/bmj.38740.439664.DE (published Feb. 1, 2006).

Campbell, N.L., et al., Use of anticholinergics and the risk of cognitive impairment in an African American population, Neurology 2010;75:152-159.

Product Information Sheet, VESIcare® (solifenacin succinate) tablets, Rev. Apr. 2010.

Product Information Sheet, SANCTURA® (trospium chloride), Rev. Jan. 2011.

Product Information Sheet, Exelon® Patch (rivastigmine transdermal system), LTS Lohmann Therapie Systems AG, 2000.

Product Information Sheet, ENABLEX® (darifenacin) tablets, T2010-XX.

Product Information Sheet, Detrol® LA (tolterodine tartrate) capsules, Rev. Mar. 2008.

Hashimoto et al, Urinary Incontinence: an Unrecognised Adverse Effect with Donepezil, The Lancet, Aug. 12, 2000, vol. 356, p. 568.

Levin et al., Direct Measurement of the Anticholinergic Activity of a Series of Pharmacological Compounds of the Canine and Rabbit Urinary Bladder, J. Urology, 1982, vol. 128(2), pp. 396-398.

Khullar et al., Presence of Faecal Incontinence among Women with Urinary Incontinence, Br. J. Obstet. Gynaecol., 1998, vol. 105, pp. 1211-1213.

Aschenbrenner et al., Drug Therapy in Nursing, 2009, pp. 1-3.

Exelon Product Sheet, Novartis, Aug. 2002, pp. 1-4.

Medline Plus. Stress Incontinence, MedlinePlus Medical Encyclopedia, 2009, pp. 1-5.

Jhee, Stanford S. et al., Centrally Acting Antiemetics Mitigate Nausea and Vomiting in Patients with Alzheimer's Disease Who Receive Rivastigmine. Clinical Neuropharmacology. vol. 25(2). pp. 122-123, Mar./Apr. 2002.

R.D. Cooke, Glycopyrrolate in Bladder Dysfunction, South African Medical Journal, Jan. 1983, vol. 63, p. 3.

\* cited by examiner

USES FOR QUATERNARY AMMONIUM ANTICHOLINERGIC MUSCARINIC RECEPTOR ANTAGONISTS IN PATIENTS BEING TREATED FOR COGNITIVE IMPAIRMENT OR ACUTE DELIRIUM

This is a divisional patent application of copending application Ser. No. 11/935,483, filed Nov. 6, 2007, entitled "NEW USES FOR QUATERNARY AMMONIUM ANTICHOLINERGIC MUSCARINIC RECEPTOR ANTAGONISTS IN PATIENTS BEING TREATED FOR COGNITIVE IMPAIRMENT OR ACUTE DELIRIUM", which claims one or more inventions which were disclosed in Provisional Application No. 60/865,893, filed Nov. 15, 2006, entitled "USE OF GLYCOPYRROLATE TO REMEDY INCONTINENCE IN PATIENTS BEING TREATED FOR COGNITIVE IMPAIRMENT OR ACUTE DELIRIUM". The benefit under 35 USC §119(e) of the United States provisional application is hereby claimed, and the aforementioned applications are hereby incorporated herein by reference.

FIELD OF THE INVENTION

The invention pertains to the field of treating patients suffering from various disorders related to various cognitive disorders. More particularly, the invention pertains to alleviating or at least improving upon adverse effects of excessive acetylcholine including, but not limited to: urinary and/or fecal incontinence, nausea, bradychardia, bronchorrhea and bronchospasm in patients being treated with certain conventional drugs for dealing with a variety of cognitive disorders, such as cognitive impairment and acute dementia. Further, improvement in cognitive function has been recognized in certain cases.

BACKGROUND OF THE INVENTION

Cognitive impairment is a serious neurological condition which is very common in the elderly. It is estimated that approximately one-third of people who live to be over 80 years of age will be diagnosed with some form of cognitive impairment, or dementia. Cognitive impairment can result from a variety of disease processes, such as, but not limited to:
  Neurodegenerative dementia:
  Alzheimer's Disease
  Pick's Disease
  Progressive Supranuclear Palsy
  Dementia with Lewy Bodies
  Parkinson's Disease
  Fronto-temporal Dementia
  Vasular Diseases:
  Stroke
  Multi-infarct dementia
  Subarachnoid hemorrhage
  Head Trauma
  Infections:
  Post-encephalitic dementia
  Syphilis
  Herpetic encephalitis
  Congenital abnormalities:
  Trisomy 21
  Toxic Brain Injuries:
  Wernike Encephalopathy
  Krorsakoff psychosis
  Alcoholic amnesic syndrome
  Alcoholic dementia The primary result of this general condition is a universal decline in the intellectual function of the individual, usually resulting in significant impediments to normal daily functions. While there is currently no disease modifying therapy available for most forms of cognitive impairment, certain therapies are available to improve cognitive functioning to varying degrees which can alleviate or at least delay the need for institutionalizing these individuals.

It has been determined that the decline of the neurotransmitter chemical acetylcholine in the brain is one of the primary mechanisms of declining mental function. Medications that can prevent or at least minimize the breakdown of acetylcholine in the brain provide significant improvement in the cognitive abilities of patients diagnosed with cognitive impairment. These medications are commonly referred to as acetyl-cholinesterase inhibitors. However, as with any medication, there are side effects. Acetyl-cholinesterase inhibitors exacerbate urinary and fecal incontinence in patients administered these drugs. Other side effects include a reduced heart rate, sweating, vasodilation and increased bronchial secretions. Such side effects may be so uncomfortable for many elderly patients that the patient is unable to tolerate effective dosing of acetyl-cholinesterase inhibitors to successfully treat the cognitive impairment.

Attempts to ameliorate these undesirable side effects in cognitively impaired patients include the administration of, for example, antimuscarinic-anticholinergic drugs (commonly called "anti-muscarinics"). These drugs block the peripheral stimulation of the acetylcholine receptors. Unfortunately, however, the use of these medications to treat the side effects of acetyl-cholinesterase inhibitors mentioned previously often contribute to cognitive impairment that is being treated. Thus, benefits of using these drugs must be balanced with the risks of exacerbating the existing cognitive impairment. As a result, many patients are either inadequately treated or go untreated.

In addition to cognitive impairment, a more severe problem often afflicts the elderly and is referred to as acute delirium. The primary indicators are a pronounced change in mental status that rapidly fluctuates, the inability to maintain normal degrees of attention, disorganized thinking and vacillating levels of consciousness. Acute delirium can often result from a severe medical illness, recent surgery and several medications or interactions between various medications. The impact of acute delirium on patients is severe and often chronic, frequently leading to death.

While the neurological mechanism by which acute delirium occurs is not completely understood, like cognitive impairment, the neurotransmitter acetylcholine is thought to play a significant role. In patients suffering from dementia, a decline in acetylcholine has been seen in post mortem studies. As with treatments for cognitive impairment, the use of acetyl-cholinesterase inhibiting medications has been determined to prevent, to varying degrees, the breakdown of acetylcholine in the brain. However, the undesired side effects outside the central nervous system that have been discussed above often result. In order to minimize these problems, the administration of drugs that block the peripheral effects of acetylcholinesterase inhibitors act would be desirable. Unfortunately, in a manner similar to other cognitive impairments, anticholinergics frequently contribute to the underlying problem by causing central nervous system toxicity.

There is thus a severe need to treat patients suffering from various forms of cognitive impairment as well as those suffering from acute delirium with an effective amount of medication to minimize or entirely alleviate these conditions without imposing upon them the undesired peripheral effects discussed previously, especially urinary and/or fecal incontinence, nausea, bradychardia, bronchorrhea and/or bronchospasm which often coexist with these cognitive impairments. The desire is to be able to administer the most efficacious type and amount of medication to treat the neurological condition without increasing the unwanted side effects of high doses of those medications. This balance has yet to be achieved in modern clinical practice.

It has been recognized that in patients suffering from incontinence, acetyl-cholinesterase inhibitors can "increase the tone of the external sphincter" (U.S. Pat. No. 5,861,431, Hildebrand et al., issued Jan. 19, 1999). The patentees note that compounds such as glycopyrrolate directly inhibit acetylcholine receptors in the bladder wall, which reduces the excessive stimulation of the bladder caused by nerves which are no longer inhibited by a normal central nervous system. Commonly assigned U.S. Pat. Nos. 6,204,285 and 6,063,808 describe the use of a single enantiomer of glycopyrrolate to treat patients suffering from urinary incontinence. They teach away from a racemic mixture of this molecule. They note that approximately 15-30% of elderly people are afflicted by urinary incontinence, but do not connect the cause of incontinence with treatments for either cognitive disorders or acute dementia.

SUMMARY OF THE INVENTION

The present invention consists of the administration of quaternary ammonium anti-cholinergic muscarinic receptor antagonists to patients being given acetyl-cholinesterase inhibitors to treat either cognitive impairment or acute delirium. The administration of the compounds of the invention prevents or substantially ameliorates the undesired side effects of acetyl-cholinesterase inhibitors, specifically adverse effects of excessive acetylcholine including, but not limited to, urinary and/or fecal incontinence, nausea, bradychardia, bronchorrhea and broncospasm. Further, the use of the compounds of the invention permits the administration of optimum therapeutic dosages of acetyl-cholinesterase inhibitors, thus maximizing the beneficial effect of the therapeutic drugs. Suitable quaternary ammonium anti-cholinergic muscarinic receptor antagonists include the drugs trospium and glycopyrrolate.

A further embodiment of administering quaternary ammonium anticholinergic muscarinic receptor antagonists to patients suffering from cognitive disorders, in general, such as dementia, acute dementia and dementia with Lewy bodies who are also being administered the acetyl-cholinesterase inhibitor rivastigmine is a resulting marked improvement in cognitive function, in addition to an improvement in controlling the adverse effects of excessive acetylcholine including, but not limited to, urinary and/or fecal incontinence, nausea, bradychardia, bronchorrhea and broncospasm.

DETAILED DESCRIPTION OF THE INVENTION

Not all antimuscarinic drugs are the same. One method of differentiating the various drugs in this category is by lipid solubility. It has been determined that quaternary ammonium compounds of the class of anti-cholinergic muscarinic agents having very low lipid solubility are desired for use within the context of this invention. As a result of their low lipophilicity (the ability of a compound to dissolve in a lipid medium), these molecules tend not to cross the blood/brain barrier as readily as those having higher lipid solubility. By not crossing this barrier, these compounds do not interfere with the normal function of acetylcholine in the central nervous system, nor do they interfere with the beneficial effects of acetyl-cholinergic inhibitors for the treatment of cognitive impairment or acute delirium. Further, these low lipid solubility quaternary ammonium antimuscarinic drugs ameliorate the undesired peripheral effects from the use of acetyl-cholinesterase inhibitors, such as urinary and/or fecal incontinence, nausea, bradychardia, bronchorrhea and broncospasm.

A benefit of using the anti-cholinergic muscarinic agents of this invention is that the maximum dosing of the acetyl-cholinesterase inhibitor to effectively treat the cognitively impaired patient can be administered or maintained.

The quaternary ammonium anti-cholinergic muscarinic agents for use with the present invention are trospium and glycopyrrolate (non-quaternary anti-cholinergic agents include, but are not limited to, oxybutinin, tolertidine, darifenacin and solefenacin). Log P, a recognized parameter proportional to octanol/water partitioning coefficient, is a standard for measuring comparative solubility of a compound in a lipid compared to water. This is the most important physical property that determines whether or not a drug molecule crosses the blood/brain barrier to interfere with the normal functioning of acetylcholine in the central nervous system. A low log P value represents low lipid solubility and low probability of crossing the blood/brain barrier. Each of these drugs has a log P based upon their chemical structure. The standard anti-muscarinic drugs in use have a log P value as high as 6.076 (tolertidine). Trospium has a log P value of 0.78 and the calculated lipophilicity of glycopyrrolate is $-75.75$, thus making them preferred compounds to achieve the therapeutic goals stated previously within the context of this invention.

The compounds of the present invention may be administered concurrently with any of the various acetyl-cholinesterase inhibitors used to treat cognitive disorders or acute delirium. Such drugs include:
donepezil
rivastigmine
galantamine
tacrine
physostigmine
pyridostigmine
neostigmine In order to treat patients suffering from cognitive impairment or acute delirium and exhibiting the unwanted adverse effects of excessive acetylcholine including, but not limited to, urinary and/or fecal incontinence, nausea, bradycardia, bronchorrea and brochospasm, it is best to combine quaternary ammonium anti-muscarinic agents with suitable acetylcholinesterase inhibitors. It is most desirable to administer both classes of drugs intravenously or intramuscularly ("parenterally") because these patients are often confused and belligerent and refuse to take oral medications. However, in some cases, oral administration may be successfully achieved.

For those patients presently exhibiting symptoms of acute delirium, in whom acetylcholinesterase inhibitor therapy is being administered, the doses are commonly: donepezil: 5-20 mg/day, galantamine: 4-24 mg/day, rivastigmine: 1.5 to 12 mg/day, physostigmine: 0.5 to 2 mg/day intravenous bolus or up to 10 mcg/minute intravenous infusion. Neostigmine and pyridostigmine have also been used, but dosing is not well defined. In order to prevent the adverse effects of excessive acetylcholine, including but not limited to, urinary and/or fecal incontinence, nausea, bradychardia, bronchorrhea and bronchospasm, glycopyrrolate can be administered at the rate of 0.1 to 0.8 mg/day parenterally or, orally, at the rate of 1 to 8 mg/day. Trospium can be administered at a rate of 20 mg twice a day.

For those patients being administered maintenance therapy for delirium, glycopyrrolate is administered concurrently with a conventional acetyl-cholinesterase inhibitor, such as donepezil hydrochloride. The dosing for glycopyrrolate is about 0.5 to 4 mg twice a day, with a dosage of about 1-2 mg twice a day most preferred. The donepezil hydrochloride is administered at a rate of about 2 to 20 mg once a day, with a dosage range of about 5 to 10 mg once a day most preferred. Rivastigmine is dosed at 1.5 to 6 mg twice each day and galantamine at 4 to 12 mg twice a day.

During the analysis of the results of clinical trials, an interesting and surprising observation was made when the acetyl-cholinesterase inhibitor rivastigmine was coupled with the quaternary ammonium anti-cholinergic muscarinic agent glycopyrrolate. It was noted that patients suffering from various forms of cognitive impairment, such as dementia, acute dementia or dementia with Lewy bodies, experienced a marked improvement in cognitive function with this specific combination of drugs. The observation was clinically significant.

The results of various trials using quaternary ammonium anti-cholinergic muscarinic agents in conjunction with acetyl-cholinesterase inhibitors are shown below in the following examples.

EXAMPLES

Example 1

Incontinence Improvement

The patients only identified by numbers below were administered an therapeutically efficacious amount of glycopyrrolate and monitored for the amount of time indicated.

| Patient | Time of treatment (months) |
| --- | --- |
| '864 | 10 |
| '105 | 7 |
| '814 | 7 |
| '124 | 8 |
| '291 | 8 |
| '547 | 8 |
| '795 | 4 |
| '104 | 6 |
| '223 | 4 |
| '970 | 4 |
| '568 | 8 |
| '255 | 6 |
| '238 | 5 |

Concurrent with the administration of glycopyrrolate, each of these patients was able to be treated with the maximum effective dosage of the acetyl-cholinesterase inhibitor donepezil, which they were unable to tolerate before treatment with glycopyrrolate because of the presence of the undesired side effects noted above. The administration of glycopyrrolate enabled the clinician to administer a dosage of acetyl-cholinesterase inhibitor that provided a measurable cognitive benefit to the patient.

Example 2

Cognitive Function vs. Incontinence

In this trial, patients were administered either of the quaternary ammonium anti-cholinergic muscarinic agents tolertidine or oxybutinin, as indicated. The patients were given a Mini-Mental State Examination (MMSE) to determine their cognitive function after being treated with either of these two drugs. The MMSE is a conventionally used test with patients suspected of exhibiting cognitive impairment. The MMSE measures an individual's cognitive ability across several domains of cognitive function. It is an acknowledged standard in the medical field and is appropriate for clinical, office based testing. It is scored from 0 to 30, with score of 30 indicating normal cognitive function.

These patients were then given a therapeutically efficacious amount of glycopyrrolate and evaluated again using the MMSE test. Their incontinence control was then evaluated and compared against treatment with tolertidine or oxybutinin only.

| Patient | Initial Drug (MMSE) | Glycopyrrolate (MMSE) | Incontinence Control |
| --- | --- | --- | --- |
| '864 | Tolertidine (14) | (18) | unchanged |
| '486 | Tolertidine (26) | (25) | improved |
| '097 | Oxybutinin (28) | (28) | improved |
| '655 | Oxybutinin (23) | (22) | improved |

The patients on the initial lipophilic anti-muscarinic agents tolertidine or oxybutinin exhibited stable cognitive function. When glycopyrrolate was administered instead, though, each patient's cognitive function remained the same but there was an improvement in three of the four subjects with respect to urinary incontinence control. The reason for this is because they were now able to take adequate doses of medication for incontinence control which did not precipitate or exacerbate the deterioration in cognitive functioning.

In a larger study, 39 patients having some form of cognitive impairment were evaluated. Their MMSE scores ranged from 13 to 29 prior to being given an acetyl-cholinesterase inhibitor. After administering this drug, their individual MMSE scores changed little, as was expected. They were then administered 1 mg twice a day of glycopyrrolate. In 64% of the patients in this group, their incontinence control improved significantly. Interestingly, incontinence control in 33% of this group declined. It is theorized that since these individuals suffered from poor mobility, such as due to hip or leg fractures, they simply could not physically reach a rest room facility in time before becoming incontinent. The incontinence of the remainder of the group remained the same.

Example 3

Rivastigmine with Glycopyrrolate

In this study, six patients with acute delirium were hospitalized and treated at Rochester (New York) General Hospital.

Patient a) Age 83. Diagnosis: Acute delirium, respiratory failure. Condition severe enough to warrant treatment in Intensive Care Unit ("ICU"). Patient was treated with a combination of rivastigmine (1.5 mg titrated to 3 mg, orally, twice each day) and glycopyrrolate (1 mg twice each day, orally). Her cognitive function improved significantly enough that she was to be discharged to a skilled nursing facility upon resolution of her respiratory issues.

Patent b) Age 77. Diagnosis: Acute delirium, urinary incontinence. Upon treatment with 1.5 mg titrated to 3 mg orally, twice a day, with rivastigmine along with 1 mg, twice a day, orally, of glycopyrrolate, the patient's cognitive function improved significantly enough to allow discharge to a skilled nursing facility.

Patient c) Age 86. Diagnosis: Acute delirium, Parkinson's disease. A regimen of 1.5 mg titrated to 6 mg, orally, twice each day, of rivastigmine and 1 mg twice each day, orally, of glycopyrrolate enabled the patient to be discharged to a skilled nursing facility in a relatively short period of time. The internist and the neurologist had no more treatment options for this patient and were looking for a long term placement in a nursing home before the above regime was administered, significantly improving his prognosis.

Patient d) Age 78. Diagnosis: Dementia with Lewy bodies, urinary incontinence. The patient was treated with a regimen of 1.5 mg titrated to 3 mg, orally, twice a day, of rivastigmine and 1 mg twice each day orally of glycopyrrolate. He showed marked improvement in 24 hours and was able to be discharge to his own home after 72 hours. Prolonged hospitalization would have been expected in the absence of the above treatment protocol.

Patient e) Age 80. Diagnosis: Acute delirium, Parkinson's disease. Patient was placed on a regimen of 1.5 mg titrated to 3 mg, orally, twice a day, of rivastigmine and 1 mg, twice each day, orally, of glycopyrrolate. Within days she showed a marked improvement in her choreoathetosis and delirium and was able to be discharged to a skilled nursing facility. She subsequently underwent uncomplicated hip surgery for a fracture, which would not have been possible without this regimen.

Patient f) Age 87. Diagnosis: Acute delirium, Extrapyramidal dysfunction. Patient was treated with 1.5 mg titrated to 3 mg, orally, twice a day of rivastigmine and 1 mg twice each day, orally, of glycopyrrolate. After only 2 days the patient showed significant improvement in cognitive function, cooperation and physical balance. His improvement was so significant that he was discharged to an assisted living level of care instead of the planned discharge to a skilled nursing facility.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for treating urinary and fecal incontinence in a patient being treated for a cognitive disorder selected from the group consisting of Alzheimer's Disease, Dementia with Lewy Bodies, Parkinson's Disease, Fronto-temporal dementia, and Progressive Supranuclear Palsy comprising administering to the patient a therapeutic amount of a quaternary ammonium anti-cholinergic muscarinic receptor antagonist.

2. The method of claim 1 wherein the quaternary ammonium anti-cholinergic muscarinic receptor antagonist exhibits low lipophilicity.

3. The method of claim 1 wherein the quaternary ammonium anti-cholinergic muscarinic receptor antagonist is selected from the group consisting of trospium and glycopyrrolate.

4. The method of claim 1 wherein an efficacious therapeutic amount of the quaternary ammonium anti-cholinergic muscarinic receptor antagonist is administered to the patient either orally, intravenously or parenterally.

5. The method of claim 1 wherein the patient is being administered acetyl-cholinesterase inhibitors for the treatment of the cognitive disorder.

6. The method of claim 5 wherein the acetyl cholinesterase inhibitors are selected from the group consisting of donepezil, rivastigmine, galantamine, tacrine, physostigmine, pyridostigmine and neostigmine.

7. The method of claim 1 wherein the quaternary ammonium anti-cholinergic muscarinic receptor antagonist is glycopyrrolate.

8. The method of claim 7 comprising administering from about 0.1 to about 0.8 mg/day parenterally, or about 3.0 to about 8.0 mg/day orally of glycopyrrolate.

9. The method of claim 5, wherein the acetyl cholinesterase inhibitor is rivastigmine and the quaternary ammonium anti-cholinergic muscarinic receptor antagonist is glycopyrrolate.

10. The method of claim 9 comprising administering from about 1.5 to about 24 mg/day orally, or about 4.6 to about 17.4 mg/day by transdermal patch of rivastigmine.

11. The method of claim 9 comprising administering the combination of from about 1.5 to about 24 mg/day, orally, or about 4.6 to about 17.4 mg/day transdermally of rivastigmine and from about 0.1 to about 0.8 mg/day, parenterally, or about 3 to about 8 mg/day, orally, of glycopyrrolate.

12. The method of claim 9 comprising administering from about 0.1 to about 0.8 mg/day parenterally, or about 3.0 to about 8.0 mg/day orally of glycopyrrolate.

13. The method of claim 9, comprising administering about 24 mg/day orally or about 17.4 mg/day transdermally of rivastigmine.

14. A method for treating urinary and fecal incontinence in a patient being treated for acute delirium comprising administering to the patient a therapeutic amount of a quaternary ammonium anti-cholinergic muscarinic receptor antagonist.

15. The method of claim 14, wherein the quaternary ammonium anti-cholinergic muscarinic receptor antagonist exhibits low lipophilicity.

16. The method of claim 14, wherein the quaternary ammonium anti-cholinergic muscarinic receptor antagonist is selected from the group consisting of trospium and glycopyrrolate.

17. The method of claim 16, comprising administering from about 0.1 to about 0.8 mg/day parenterally, or about 3.0 to about 8.0 mg/day orally of glycopyrrolate.

18. The method of claim 14, wherein the patient is being administered acetyl-cholinesterase inhibitors for the treatment of acute delirium.

19. The method of claim 18, wherein the acetyl cholinesterase inhibitor is rivastigmine and the quaternary ammonium anti-cholinergic muscarinic receptor antagonist is glycopyrrolate.

20. The method of claim 19 comprising administering the combination of from about 1.5 to about 24 mg/day, orally, or about 4.6 to about 17.4 mg/day transdermally of rivastigmine and from about 0.1 to about 0.8 mg/day, parenterally, or about 3 to about 8 mg/day, orally, of glycopyrrolate.

* * * * *